United States Patent [19]

Wilhelms

[11] Patent Number: 5,116,731

[45] Date of Patent: May 26, 1992

[54] PROCESS FOR THE DETECTION OF AN ALLERGY OR AN ANTI-ALLERGIC SUBSTANCE

[75] Inventor: Otto-Henning Wilhelms, Weinheim-Rittenweier, Fed. Rep. of Germany

[73] Assignee: Boehringer Mannheim GmbH, Mannheim, Fed. Rep. of Germany

[21] Appl. No.: 349,983

[22] Filed: May 9, 1989

Related U.S. Application Data

[63] Continuation of Ser. No. 807,259, Dec. 10, 1985, abandoned.

[30] Foreign Application Priority Data

Dec. 21, 1984 [DE] Fed. Rep. of Germany ....... 3446714

[51] Int. Cl.$^5$ .............................................. C12Q 1/34
[52] U.S. Cl. ...................................... 435/18; 435/23; 435/29; 435/219; 435/226; 435/7.24; 436/513; 436/519; 436/809; 436/811
[58] Field of Search ............... 435/18, 23, 29, 219, 435/226, 7.24; 436/513, 519, 809, 811; 422/61

[56] References Cited

U.S. PATENT DOCUMENTS

| | | | |
|---|---|---|---|
| 4,016,042 | 4/1977 | Svenden | 435/23 |
| 4,028,318 | 6/1977 | Aurell et al. | 530/330 |
| 4,162,941 | 7/1979 | Aurell et al. | 435/23 |
| 4,252,715 | 2/1981 | Aurell et al. | 530/330 |
| 4,278,763 | 7/1981 | Berger et al. | 435/23 |
| 4,279,617 | 7/1981 | Masson et al. | 436/513 X |
| 4,457,866 | 7/1984 | Karges et al. | 530/329 |
| 4,487,155 | 5/1984 | Ryan et al. | 546/159 |
| 4,559,310 | 12/1985 | Cantor et al. | 436/513 |
| 4,592,997 | 6/1986 | Wilhelms et al. | 435/23 |

OTHER PUBLICATIONS

Boehringer Mannheim Biochemical Catalogue 1984,85, p. 42.
Römpps chemie-Lexikon (1981), p. 818.
E.-C. Witte, Arzneim.-Forsch., Drug Res. 39 (II), Nr. 10a (1989) p. 1309.
Wilhelms, O. H. and E. Roesch Allergologie, vol. 7 Nr. 7 pp. 49–59 (German) pp. 52–53 (English).
B. Gruber et al. Clin. Exp. Immunol. (1988) 71, 289–294.
Jurgen Bommer et al. Kidney International vol. 26 (1984) pp. 331–337.
Assem, E. S. K. et al. Br. J. Radiology (1983) 56:647–652.
D. Vervloet, Clin. Allergy 15:501–508 (1985).
Henrik Permin et al. (1978) Allergy 33:15–23.
Henrik Permin et al., (1983) Allergy 38:273–281.
J. Bommer et al. (1985) The Lancet Dec. 21/28 pp. 1382–1385.
Ivan M. Roitt et al., Immunology (1989) Gower Medical Publishing London-New York, pp. 19.1–19.2, 19.10–19.13.

Primary Examiner—Esther L. Kepplinger
Assistant Examiner—Carol A. Spiegel
Attorney, Agent, or Firm—Felfe & Lynch

[57] ABSTRACT

The present invention provides a one-step process for the detection of the presence of an allergy and for the specific detection of the allergen responsible for the allergy, in which the leukocytes of a sample to be investigated are incubated with an allergen or with another stimulation factor in an aqueous medium together with a chromogenic protease substrate and calcium ions, the liberated protease is reacted with the chromogen and the resulting chromophor is determined. The protease activity is measured kinetically after an incubation period by the increase of the chromophor concentration. The present invention also provides a reagent and a device for carrying out this process, as well as a process for the determination of antiallergic and anti-inflammatory substances. The device consists of a microtiter plate with a plurality of different reagents arranged in rows.

26 Claims, No Drawings

PROCESS FOR THE DETECTION OF AN ALLERGY OR AN ANTI-ALLERGIC SUBSTANCE

This application is a continuation of application Ser. No. 807,259, filed Dec. 10, 1985 now abandoned.

The present invention is concerned with an improved process for the detection of the presence of an allergy and for the specific detection of the allergen responsible for the allergy. This process can also be used for the diagnosis of other diseases, in the pathomechanism of which a stimulus-induced liberation of mediators from mast cells and basophils participates. Furthermore, the process can be used for an automatable screening process for pharmaceuticals which suppress the stimulus-induced mediator liberation from basophils, mast cells and phagocytes and thus can be used for a therapy of allergic or inflammatory diseases.

In the case of allergy patients, an increased IgE level is found in the blood. Furthermore, IgE is found bound to mast cells and basophils. The allergic reaction is initiated by the binding of the specific allergen on to cell-bound IgE molecules specific therefor.

It is frequently assumed that this binding of the stimulating allergen to IgE via the so-called bridging of neighbouring IgE brings about, in a complex reaction, the degranulation of basophilic leukocytes. As is known, the degranulation liberates histamine, proteases, metabolites of arachidonic acid, phosphatases and other enzymes.

In Federal Republic of Germany Patent Specification No. 31 47 763, for the diagnosis of allergic diseases, it is suggested to separate the blood of possibly allergic persons into a plasma layer containing the white blood corpuscles and into a layer with the red blood corpuscles, to recover the plasma layer, to mix with an indicator solution and to retain a part as control and to mix a part with the allergen(s) to be tested. After a more or less long incubation time, the indicator reaction is determined either directly or photometrically after the addition of further reagents, the enzyme activity being determined by comparison with the initial values or the value of the control solution. As enzymes possibly to be measured, there are mentioned proteases and alkaline phosphatase which are to be activated by the allergic reaction. Difficulties are caused in the case of this process because allergens, which themselves display a protease or phosphatase activity, cannot be detected with this test and, on the other hand, even the serum of healthy subjects display a certain degree of protease and phosphatase activity and the control solution thereby also displays a reaction which must be deducted from that of the measurement solution in order to obtain the value specifically brought about by the allergy which, as is known, leads to a considerable breadth of error.

Therefore, in Federal Republic of Germany Patent Specification No. 32, 11 254, it is suggested, in analogy to the known fluorimetric histamine liberation test, to separate the leukocytes from the serum, to remove adhering serum residues by repeated washing with an appropriate buffer solution and to resuspend the cells again in such a buffer. The so obtained suspension is thereafter mixed with an allergen or with a solution of anti-IgE antibodies and, in a further step, by the addition of a calcium chloride solution, the liberation of histamine or protease is stimulated. After a definite incubation time, the reaction is stopped by the addition of a solution of ethylenediamine-tetraacetic acid (EDTA), the cells are sedimented and in the supernatant, instead of the previously known, laborious fluorimetric measurement of histamine, by the addition of an indicator solution, the protease activity liberated by the allergen is measured. Thus, the process can be carried out without apparatus or with the use of simple photometer. Although this process is substantially less subject to disturbance than the fluorimetric histamine measurement, due to the necessary number of process steps, it proves to be laborious for a routine test.

Therefore, it is an object of the present invention to provide a process for the diagnosis of allergic diseases by means of which the above-mentioned cellular reaction on allergens can be carried out more simply and quickly and, if possible, the sensitivity of the detection reaction is also increased. Therefore, the process principle should also be suitable for the diagnosis of other diseases, for example, of rheumatic arthritis, of pharmaceutical supersensitivity (e.g. penicillin incompatibility) or of incompatibility in the case of patients requiring dialysis, in the pathomechanism of which a stimulus-induced mediator liberation from basophils and mast cells participates.

Thus, according to the present invention, there is provided a process for the detection of the presence of an allergy and for the specific detection of the allergen responsible for the allergy, in which leukocytes of a sample to be investigated are incubated with a natural or synthetic allergen or with another stimulation factor, such as anti-IgE antibody, RNA, DNA or immune complexes, in an aqueous medium, the liberated protease is reacted with a chromogen and the resulting chromophor is determined, wherein the allergen or an other stimulant is mixed in a buffer with a pH of 6.3 to 9 with 0.5 to $5 \times 10^{-3}$ mol/l. of calcium ions and $10^{-4}$ to $10^{-3}$ mol/l. of chromogen in isotonic solution and mixed with $10^9$ to $10^{10}$ of the leukocytes to be investigated per liter and the protease activity is measured kinetically after an incubation period by the increase of the chromophor concentration.

Analogously, for the detection of a rheumatic arthritis, there is used the liberation of protease after the addition of cell nucleus parts of eukaryotic cells, especially DNA, RNA or immune complexes to the leukocyte suspension.

Furthermore, the present invention provides a reagent for carrying out the above process, which comprises a buffer with a pH of from 6.3 to 9, an allergen or other stimulant in an amount of from 0.01 to 100 mg./l., a calcium salt in a concentration of from 0.5 to $5 \times 10^{-3}$ mol/l. and chromogen in a concentration of $10^{-4}$ to $10^{-3}$ mol/l.

The present invention also provides a device for the detection of allergies or corresponding stimulation factors, as well as for the determination of antiallergic substances, comprising a microtitre plate which contains, arranged in rows, different reagents according to the present invention with anti-IgE antibodies or various allergens or other stimulants in various concentrations, the same reagent mixtures optionally being provided in several positions for obtaining average values.

In addition, the present invention provides a process for the determination of antiallergic and antiinflammatory substances, wherein a reagent according to the present invention is mixed, in a process according to the present invention, with a pharmaceutical and leukocytes are added thereto which are sensitive towards the allergen or further stimulants (anti-IgE antibodies, opsonised zymosan) and the reaction weakened in comparison with a control is measured.

Since only small amounts of reagent and test substances (0.2 to 1 ml. per sample) are needed for the reaction, the reaction can preferably be carried out on a microtitre plate, the reagents thereby preferably being present in a solid and especially lyophilised from and in a definite amount in the compartments of the microtitre plate, the reaction solution being reconstituted by the addition of the leukocyte suspension. The reagents can also be impregnated on to an absorbent carrier, for example, a paper, synthetic resin or glass fibre fleece, a swellable synthetic resin film or a gel and introduced in this form into a reaction vessel. However, the impregnated carrier can also be moistened directly with the leukocyte suspension and brought to reaction in the manner usual for other dry chemical reactions. The chromogenic reaction can be measured either visually or, in the case of higher requirements for exactitude, with a photometer. For the throughput of larger numbers of samples, this process can, of course, be automated in known manner. Therefore, the process is also especially appropriate for the pharmaceutical screening of antiallergic compounds which inhibit the stimulus-induced degranulation of mast cells and basophils. The same test principle can also be used for the detection of enzyme liberation from phagocytizing cells after the addition of, for example, opsonised zymosan and thus for the discovery of inflammation-inhibiting substances.

It is surprising that it is possible to place all the reagents necessary for the liberation and detection of a protease in a uniform mixture and merely to add thereto the leukocyte suspension in a simple pipetting step since, on the one hand, the indicators in the hitherto usual concentration of $10^{-2}$ to $10^{-3}$ mol/l. bring about a spontaneous liberation of protease from leukocytes if this reaction is not previously inhibited by the addition of chelating agents, such as EDTA, and, on the other hand, it was known that it is not possible to add the calcium or magnesium ions necessary for the liberation of the protease from the basophilic leukocytes before the addition of the stimulating allergens to the leukocyte solution since the calcium ions, in this case, bring about a change of the leukocyte membrane which inhibits the attack of the allergen.

However, as we have now found, the addition of the chromogens in an amount of from $10^{-4}$ to $10^{-3}$ mol/l. either does not bring about a non-specific, spontaneous liberation of protease or only such a small liberation that it does not disturb the test. On the other hand, by means of this addition, the protease liberated by the allergen is, surprisingly, stabilised in an as yet unknown manner so that, in the case of the addition of the same amount of allergen, a markedly high protease activity is measured in comparison with the previously known reactions. It is assumed that, in the case of the simultaneous addition of allergen and calcium ions, the allergens bind so quickly to the active places of the cell membrane that a reduction of the reactivity due to the calcium ions does not occur and these merely catalyse the desired protease transport through the cell membranes.

The following statements for the carrying out of the process apply generally to all its variants. They are illustrated using the example of the use of the process for the diagnosis of an allergy. For the process according to the present invention, depending upon the nature of the allergen and the severity of the allergic reaction, the allergens are used in an amount of from 0.01 to 100 mg./l. and especially of from 1 to 10 mg./l. of reaction solution.

Calcium ions, as well as possibly magnesium ions, are used advantageously in a concentration of from 0.5 to $5 \times 10^{-3}$ mol./l. and especially of from 3 to $4 \times 10^{-3}$ mol/l. These ions are usually employed in the form of water-soluble salts and especially as chlorides, sulphates, acetates or citrates.

The reaction is carried out in a solution buffered to a pH of 6.3 to 9, preferably of 7.0 to 8 and especially of 7.5. The buffer used is preferably the same buffer which is used for washing and suspending the leukocytes, i.e. a physiological buffer which, by the addition of sodium chloride, potassium chloride, glucose or other physiologically compatible substances, is made isotonic and has a concentration of about $5 \times 10^{-3}$ to $10^{-1}$ mol/l. of buffer substance. The buffer substances which can be used include tris buffer, phosphate buffer, glycine buffer and other physiologically compatible buffers, or possibly also mixtures of buffers, the buffer capacity of which can be adjusted to the above-mentioned pH range and which, in the above-given concentrations, do not form insoluble salts with the calcium or magnesium ions. In the scope of the present invention, these buffer systems are also called "buffers".

For the stabilisation of the leukocytes, this solution can additionally also contain gelatin or other macromolecular materials with cell-stabilising properties, such as are well known.

The reaction is usually carried out between ambient temperature and 37° C., the physiological conditions corresponding to a temperature of 35° to 37° C. being preferred. In the case of this temperature, after 15 to 60 minutes incubation, normally so much proteinase is liberated that the measurement can take place. However, in the case of a smaller allergen concentration and a weaker liberation reaction, the incubation time can be increased. In this case, the measurement reaction is preferably carried out at ambient temperature since the enzymes, as we have ascertained, are stable at this temperature even over comparatively long periods of time (over 100 hours) and give a linear reaction kinetic. In the case of a stronger liberation reaction, care must be taken that no chromogenic substrate impoverishment occurs because otherwise the colour reaction no longer proceeds linearly. In these cases, a measurement at 37° C. accelerates the enzyme reaction. However, measurements can also be advantageously carried out at ambient temperature.

Because of the simple carrying out of the process, which only requires one pipetting step for the addition of the leukocytes to the finished reagent mixture, the process according to the present invention is especially suitable for a large series of experiments in which the sensitivity of a given leukocyte suspension towards various allergens or other stimuli is to be tested and, on the other hand, in order to test unknown substances for an antiallergic action. These substances are thereby admixed either with the reagent or with the leukocyte suspension in appropriate concentration and the reduction of the protease liberation is determined in comparison with a control solution not mixed with the substance in question.

As chromogenic substances (substrates) according to the present invention, there can be used all those which react in the pH range used according to the present invention with protease and produce a visually, photometrically or also fluorimetrically detectable product.

Substrates which can be used include, for example, N-benzoylarginine-p-nitroanilide, N-(3-carboxypropionyl)-phenylalanine-p-nitroanilide or p-nitroanilides substituted by peptides, such as are described, for example, in Federal Republic of Germany Patent Specifications Nos. 25 27 932; 25 52 570; 2629 067 and 32 11 254. Other reagents with chromophoric or fluorescing residues, which are substituted by peptides which can be split off, are described in Federal Republic of Germany Patent Specifications Nos. 29 36 543; 30 17 721 and 28 54 987 and in European Patent Specification No. 0,078,703. By chromogen in the sense of the present invention, there is to be understood not only the substrate itself but also the other reagents possibly also necessary for the formation of colour forming, such as are described, for example, in the above-mentioned Patent Specifications. Especially mentioned are reaction accelerators, stabilisers, oxidation adjuvants, colour couplers, contrast colour agents, viscosity-regulating materials and wetting agents.

The following Examples are given for the purpose of illustrating the present invention:

EXAMPLE 1

1.1 Obtaining Leukocytes 60 ml. of venous blood from a donor were carefully mixed with 30 ml. of a dextran mixture (dextran with an average molecular weight of 75,000 2%; D-glucose 2%; EDTA 20 mmol/l.; gelatin 0.07%) in a polyethylene beaker and transferred to a siliconised separating funnel. After leaving standing for 60 to 90 minutes at ambient temperature, the supernatant containing the leukocytes (about 50 ml.) was separated off and mixed with 50 ml. tris buffer of pH 7.6 (tris 22 mmol/l.; sodium chloride 0.12 mol/l.; potassium chloride 5 mmol/l.; gelatin 0.05% EDTA 1 mmol/l.; D-glucose 0.1%) and centrifuged for 15 minutes at 800 g. After decanting, the cells were washed twice in that, in each case, they were again suspended with 50 ml. of the same buffer mixture of pH 7.6 and, in each case, centrifuged for 15 minutes at 800 g. The cells were suspended in 10 ml. of the same buffer mixture and, by dilution with further buffer, adjusted to $10^7$ cells/ml.

1.2 Reagent Mixture 10 ml. Anti-IgE solution (Behring Werke No. OTNP 04/05 diluted 1:500 with tris buffer of pH 7.6 as in 1.1)

10 ml. calcium chloride solution (4 mmol/l. in isotonic sodium chloride solution, pH 7.6)

20 ml. chromozyme ® TH (tosyl-glycyl-propyl-arginine-4-nitroanilide-acetate) solution 0.75 mmol/l (one bottle Boehringer Mannheim GmbH, Order No. 199664 dissolved in 10 ml. water) were thoroughly mixed and stored until used.

1.3 Proteinase Stimulation With Anti-IgE Antibodies (Table I)

0.5 ml. amount of leukocyte suspension were added to 0.5 ml. of the reagent mixture, incubated at 37° C. and the extinction measured at 405 nm after 45, 90 and 180 minutes.

In order to determine the non-specific decomposition, there was carried out a corresponding control without the addition of anti-IgE but with all the other components of the reagent solution. From the extinction differences between measurement and control solution (Table I), there can be determined the proteinase liberation from the leukocytes by the stimulant.

TABLE I

Proteinase Liberation from Leukocytes by Anti-IgE Antibodies

| average values from 3 measurements | 45 min. | 90 min. | 180 min. |
|---|---|---|---|
| a) Blood from non-allergic subjects | | | |
| control | 0.015 | 0.042 | 0.097 |
| anti-IgE | 0.062 | 0.170 | 0.382 |
| $\Delta E_{405}$ | 0.047 | 0.128 | 0.285 |
| b) Blood from allergic subjects (hay fever) | | | |
| control | 0.025 | 0.058 | 0.122 |
| anti-IgE | 0.305 | 0.857 | 1.743 |
| $\Delta E_{405}$ | 0.280 | 0.799 | 1.621 |

1.4 Protease Stimulation With Grass Allergens (Table II)

Under the same conditions as under 1.3 above but with a reagent which contains 10 ml. allergen extract from grass pollen ($10^{-5}$ g./ml. allergen in tris buffer of pH 7.6 according to 1.1 above), blood samples from healthy and allergic subjects were compared.

TABLE II

Protease Stimulation With Grass Allergens

| average values from 3 measurements | 45 min. | 90 min. | 180 min. |
|---|---|---|---|
| a) Blood from non-allergic subjects | | | |
| control | 0.018 | 0.037 | 0.092 |
| allergen | 0.037 | 0.045 | 0.109 |
| $\Delta E_{405}$ | 0.019 | 0.008 | 0.017 |
| b) Blood from allergic subjects (hay fever) | | | |
| control | 0.020 | 0.048 | 0.082 |
| allergen | 0.180 | 0.424 | 0.864 |
| $\Delta E_{405}$ | 0.160 | 0.376 | 0.782 |

1.5 Interpretation of Results

It is shown in Table II above from a comparison of the reactions that the non-specific coloured material formation brought about by the buffer is clearly smaller than that brought about by liberated protease.

Anti-IgE antibodies also bring about a certain protease liberation with the leukocytes of healthy subjects which, however, is weaker than in the case of allergic subjects so that this test can be used as a non-specific test for allergic reactions.

The weak reaction of normal leukocytes towards allergens differs, in turn, significantly from the strong reaction of allergised leukocytes, which makes possible a satisfactory determination of the allergens.

EXAMPLE 2

Influence Of The Addition Of Calcium Ions On The Histamine And Proteinase Liberation (Table III)

For the demonstration of the influence of the sequence of the addition of the reagents, the test described in Example 1.3 a) was repeated but the reagent components according to Example 1.2 were added in the following sequence:

a) 0.5 ml. of cell suspension according to Example 1.1 was mixed with 0.125 ml. calcium chloride solution and, after 10 minutes, 0.125 ml. anti-IgE solution was added thereto.

b) 0.5 ml. cell suspension was mixed with a mixture of 0.125 ml. calcium chloride solution and 0.125 ml. anti-IgE solution.

c) 0.5 ml. cell suspension was mixed with 0.125 ml. anti-IgE reagent solution and, after 1 minute, 0.125 ml. calcium chloride solution added thereto.

As control, in each case, 0.5 ml. of TRIS buffer was mixed in the same way with the reagent solutions.

All the batches were incubated for 60 minutes at 37° C., the proteinase liberation was stopped by the addition of 0.5 ml. EDTA solution (0.1 mol/l. in 0.15M tris buffer of pH 7.6) and the cells were centrifuged off. In the cell-free supernatant, the liberated histamine was measured by automated fluorimetry and, in a separated part, by the addition of chromozyme TH ($5 \times 10^{-4}$M), there was measured photometrically the protease activity liberated after a further 60 minutes at 37° C. The values set out in the following Table III were determined from 3 to 6 measurements.

TABLE III

Inhibition of histamine and Proteinase liberation by Premature Addition of Calcium Ions

| | histamine % of total content | | | proteinase ($\Delta$ E$_{405}$) | | |
|---|---|---|---|---|---|---|
| | a | b | c | a | b | c |
| control | 7 | 4 | 6 | 0.040 | 0.016 | 0.017 |
| sample | 14 | 40 | 35 | 0.084 | 0.271 | 0.227 |
| difference | 7 | 36 | 29 | 0.044 | 0.255 | 0.210 |

This experiment clearly shows that a premature addition of calcium chloride inhibits the liberation.

EXAMPLE 3

Influence Of The Chromogen Addition Of The Histamine And Proteinase Liberation (Table IV)

In order to demonstrate the influence of the chromogen addition, the following experiments were carried out:

a) 0.5 ml. cell suspension was mixed with a mixture of 0.125 ml. calcium chloride solution and 0.125 ml. anti-IgE solution. After incubation for 60 minutes at 37° C., the reaction was stopped with 0.125 ml. EDTA solution. After centrifuging, the histamine and proteinase content was determined in the supernatant. The proteinase was measured by the addition of 0.125 ml. chromozyme TH solution, further incubation for 60 minutes at 37° C. and measurement of the extinction difference at 405 nm.

b) 0.5 ml. cell suspension was mixed with 0.5 ml. reagent according to Example 1.2, incubated for 60 minutes at 37° C., the histamine content was determined in a cell-free part and a first extinction value was measured at 405 nm. After further incubation at 37° C. for 60 minutes, a second extinction was measured and the proteinase content determined from the extinction increase.

c) In a further batch, the operation was as described under a) but the cells were not separated from the sample serving for the proteinase determination.

TABLE IV

Stabilization of liberated Proteinase by Chromogen

| | histamine % | | | proteinase ($\Delta$ E$_{405}$) | | |
|---|---|---|---|---|---|---|
| | a | b | c | a | b | c |
| control | 4 | 11 | 6 | 0.02 | 0.07 | 0.03 |
| sample | 24 | 40 | 35 | 0.18 | 0.51 | 0.20 |
| difference | 20 | 29 | 29 | 0.16 | 0.44 | 0.17 |

It is shown from a comparison of the above measurement values that test variant b) gives a clearly stronger proteinase measurement signal than in the case of c), whereas the histamine liberation is about equally high. It is concluded from this that, in the presence of the chromogenic substrate, the liberated proteinase is stabilised or is protected from inactivation by other test components.

EXAMPLE 4

Comparison Of The Allergen- And Anti-IgE-Induced Proteinase Liberation From Leukocyte Suspensions Of Various Subjects With Suspected Allergy (Table V)

Measurement example in microtitre plate: 0.3 ml. batches ~$1.4 \times 10^7$ cells/ml. (microtitre plates Nunclon 96U).

Concentrations: various allergens 10 $\mu$g./ml.; anti-IgE antibody solution: 1:8000 dilution, other reagents as in Example 3.

Proteinase activity: absolute $\Delta$E$_{405}$, measured 50 and 110 minutes after the addition of the stimuli without cell separation with a Dynatech Microelisa Autoreader MR 580.

TABLE V

Comparison of the Allergen and Angi-IgE Induced Proteinase liberation from Leukocyte Suspensions of Subjects with Suspected Allergy

| | c | IgE | gp | hn | bp | mts | | c | IgE | gp | hn | bp | mts |
|---|---|---|---|---|---|---|---|---|---|---|---|---|---|
| A | 0.25 | .170 | .147 | .058 | .165 | .030 | C | .015 | .085 | .033 | .025 | .033 | .022 |
| | .032 | .180 | .163 | .070 | .155 | .040 | | .018 | .095 | .043 | .028 | .039 | .027 |
| | .018 | .177 | .154 | .066 | .168 | .037 | | .013 | .098 | .037 | .029 | .027 | .029 |
| | .039 | .187 | .170 | .084 | .175 | .054 | | .022 | .087 | .033 | .031 | .026 | .015 |
| B | .037 | .110 | .042 | .100 | .080 | .030 | D | .010 | .220 | .170 | .015 | .130 | .240 |
| | .027 | .105 | .040 | .095 | .090 | .025 | | .017 | .205 | .185 | .025 | .135 | .235 |
| | .045 | .103 | .026 | .092 | .095 | .038 | | .019 | .235 | .165 | .022 | .138 | .224 |
| | .047 | .122 | .045 | .087 | .094 | .024 | | .025 | .217 | .175 | .027 | .125 | .238 |

The above Table V shows the measurement values of 4 subjects (blocks A–D), lines 1–4 and 5–8 in each case showing parallel measurements. The results for patients in the above table are actually net values since control binding has been substracted out. Columns 1 and 7 show the control values with buffer solution (c), columns 2 and 8 the inducing with anti-IgE antibodies (IgE), columns 3 and 9 with allergen extract from grass pollen (gp) (Allergopharma Ganzer KG, Order No. 006), columns 4 and 10 allergen extract from hazelnut (hn) (Allergopharma Ganzer KG, Order No. 012), columns 5 and 11 allergen extract from birch pollen (bp) (Allergopharma Ganzer KG, Order No. 013) and columns 6 and 12 allergen extract from mites (mts) (Allergopharma Ganzer KG, Order No. 725). The reaction with anti- IgE antibodies of subjects A, B and D, indicates an existing allergy.

Subject A shows a clearly allergic reaction with grasses (gp) and birch pollen (bp). Subject B shows a reaction of average strength with both tree pollens (hn, bp). Subject D reacts sensitively to grasses (gp) and birch (bp) and very strongly to mite (mts) allergens. Only in the case of hazelnut is no significant reaction to be seen.

The suspected allergy from the anti-IgE reaction is confirmed by the allergen-specific reactions of subjects A, B and D.

Subject C reacts clearly more weakly with anti-IgE and practically not at all with allergens so that he is not an allergic subject.

EXAMPLE 5

Inhibition Of The Anti-IgE-Induced Proteinase Liberation From A Pooled Leukocyte Suspension Of Healthy Subjects (n=4) With Various Standard Substances Table VI In a microtitre plate (Nunclon 96U) with 8×12 vessels, in each case there was placed 0.1 ml. leukocytes prepared according to Example 1.1 (about $1.2 \times 10^7$ cells/ml.). and in each case 4 vessels were supplied with 0.1 ml. of the substrate solution to be tested in the concentrations given below. Thereafter, 0.1 ml. reagent solution of $5 \times 10^{-4}$M chromogyme® TH and $3 \times 10^{-3}$M calcium chloride, 0.15M tris buffer of pH 7.6 in isotonic solution of sodium chloride was added thereto, incubated at 37° C. and, after 45 minutes and 140 minutes, without cell separation, the extinction was measured with a Dynatech Microelisa Autoreader NR 580 at 405 nm. Concentrations of the substrates referred to the total batch:

theophylline: $10^{-3}$M, $2 \times 10^{-4}$M, $4 \times 10^{-5}$M
papaverine: $10^{-4}$M, $2 \times 10^{-5}$M, $4 \times 10^{-6}$M
cromoglycate: $5 \times 10^{-4}$M, $10^{-4}$M, $2 \times 10^{-5}$M
iodoacetate: $5 \times 10^{-3}$M, $10^{-3}$M, $2 \times 10^{-5}$M
2,4-dinitrophenol: $5 \times 10^{-5}$M, $10^{-5}$M
picumast: $5 \times 10^{-5}$M, $10^{-5}$M, $2 \times 10^{-6}$M
chromoglycate i.e. chromoglycic acid is the generic name for the anti-allergic substance 5,5'-(2-hydroxy-trimethylendioxy)-bis(4-oxochromen-2-carbonicacid). Picumast is the generic name for 3,4-demethyl-7-[4-(4-chlorobenzyl) piperazine-1-yl]propoxycoumarine.

TABLE VI

Inhibition with Various Standard Substances of the Anti-IgE induced Proteinase Liberation from a pooled Leukocyte Suspension of Healthy Subjects

| buffer | Theophylline | | | Cromoglycate | | | Isoprenaline | | | 2,4-Dinitrophenol | |
|---|---|---|---|---|---|---|---|---|---|---|---|
| | 1 | 2 | 3 | 1 | 2 | 3 | 1 | 2 | 3 | 1 | 2 |
| .015 | .032 | .075 | .172 | .190 | .175 | .199 | .135 | .170 | .190 | .065 | .155 |
| .025 | .037 | .069 | .178 | .170 | .195 | .195 | .141 | .165 | .182 | .055 | .135 |
| .018 | .028 | .064 | .184 | .189 | .187 | .184 | .146 | .173 | .195 | .061 | .147 |
| .022 | .029 | .062 | .182 | .192 | .188 | .189 | .134 | .185 | .193 | .070 | .142 |
| .185 | .035 | .067 | .180 | .047 | .171 | .207 | .190 | .029 | .091 | .160 | .023 |
| .195 | .025 | .069 | .171 | .067 | .161 | .202 | .180 | .027 | .071 | .177 | .028 |

TABLE VI-continued

Inhibition with Various Standard Substances of the Anti-IgE induced Proteinase Liberation from a pooled Leukocyte Suspension of Healthy Subjects

| papaverine | | | Picumast | | | iodoacetate | | | buffer |
|---|---|---|---|---|---|---|---|---|---|
| 1 | 2 | 3 | 1 | 2 | 3 | 1 | 2 | 3 | |
| .200 .030 | .082 | .173 | .053 | .154 | .184 | .195 | .031 | .077 | .169 .031 |
| .189 .037 | .076 | .165 | .055 | .163 | .209 | .176 | .022 | .079 | .172 .015 |

(anti-IgE)

It is shown see Table VI that, as antiallergically-active known substances, also in the new test arrangement, a clearly, partly concentration-dependent inhibition action is obtained. In the same way, energy metabolism blockers, such as dinitrophenol or iodoacetate, also pron.ote the proteinase liberation but not, according to expectation, the $\beta$-stimulators isoprenaline or cromoglycate. The test is thus well suited for the serial investigation of such substances.

EXAMPLE 6

Detection of Allergens With Test Strips

Filter paper (Schleicher & Schüll No. 2352) was impregnated with the following mixture, dried at 60° C. and cut up into 10 mm. wide strips.
15 mmol TRIS [2-amino-2-(hydroxymethyl)-1,3-propandiol] buffer (pH 8.0)
130 mmol sodium chloride
0.2 g. gelatin (M.W. about 10,000)
50 mg. allergen mixture (grasses, trees, mites)
2 mmol calcium chloride
6 mmol glucose
1 mmol indicator (dissolved in 10 ml. acetone)
5 mmol phosphoric acid trimorpholide
2 g. decanol
add 1 liter water.

As indicators, 3-(N-succinyl)-L-alanyloxyindole, 3-(N-toluenesulphonyl-L-alanyloxy)-indole and 3-(N-(toluene-4-sulphonyl)-L-valyloxy)-indole are used with the same result.

These strips were so sealed in, by means of hot rollers, between a 60 mm. wide band of melt wax-coated polyester foil and a 20 mm. wide band of polyester fleece (15 g./m²) that the middle of the test paper came to lie 6 mm. from the lower edge of the polyester band and under the middle of the fleece band, the hot rollers used having a recess at the position of the test paper. The finished sealed band was then cut transversely into 6 mm. wide strips.

When these strips are dipped into a suspension according to Example 1 containing about $10^7$ leukocytes/ml., then, in the case of leukocytes from allergic subjects, after 15 to 30 minutes, blue to dark blue coloured papers are obtained. With leukocytes of healthy subjects or with pure buffer solution, the papers do not colour or only achieve a pale blue colour. The coloration can possibly also be measured by reflectometry.

It will be understood that the specification and examples are illustrative but not limitative of the present invention and that other embodiments within the spirit and scope of the invention will suggest themselves to those skilled in the art.

What is claimed is:

1. A process for the detection of an allergy produced by foreign or self-antigens wherein an allergy-specific protease is liberated from mast cells and basophils in response to a degranulation factor specific for said allergy comprising incubating a suspension containing $10^9$ to $10^{10}$ human leukocytes per liter with said allergy-specific degranulation stimulation factor for a period of time sufficient to liberate said allergy-specific protease wherein the incubation is carried out in an aqueous medium containing a buffer with a pH of from 6.3 to 9, and 0.5 to $5 \times 10^{-3}$ mol/l of calcium ions and $10^{-4}$ to $10^{-3}$ mol/l of a chromogen in isotonic solution wherein said chromogen specifically reacts with the liberated allergy-specific protease to form a chromophor, determining the liberation of allergy-specific protease by kinetically measuring formation of said chromophor, and detecting thereby the presence of said allergy.

2. The process of claim 1 wherein said degranulation stimulation factor is an allergen.

3. A process for the detection of the presence of an allergy-specific degranulation stimulation factor responsible for liberating an allergy-specific protease from mast cells and basophils in response thereto, comprising incubating said allergy-specific degranulation stimulation factor with a sample having $10^9$ to $10^{10}$ human leukocytes per liter to liberate said allergy-specific protease, the incubation being carried out in an aqueous medium containing a buffer with a pH of from 6.3 to 9 and 0.5 to $5 \times 10^3$ mol/l of calcium ions and $10^{-4}$ and $10^{-3}$ mol/l of chromogen in isotonic solution wherein said chromogen specifically reacts with the liberated allergy-specific protease to form a chromophor, kinetically determining formation of said chromophor, and thereby detecting the presence of said allergy-specific degranulation stimulation factor.

4. The process of claim 1 or 2 wherein the buffer concentration is $5 \times 10^{-3}$ to $10^{-1}$ mol/l and has a pH value of 7 to 8.

5. The process of claim 4 wherein the allergy-specific degranulation stimulation factor is added in an amount of 0.01 to 100 mg/l.

6. The process of claim 5 wherein the allergy-specific degranulation stimulation factor is anti-IgE antibody.

7. The process of claim 4 wherein the buffer is selected from the group consisting of tris, phosphate and glycine buffers.

8. The process of claim 4 wherein the aqueous medium additionally contains magnesium ions.

9. The process of claim 6 wherein the anti-IgE antibody is present in an amount of 0.01 to 100 mg/ml.

10. The process of claim 1 wherein the allergy-specific degranulation stimulation factor consists of self-antigens consisting of DNA, RNA or immune complexes.

11. The process of claim 10 wherein the allergy-specific degranulation stimulation factor is RNA or DNA.

12. The process of claim 1 or 3 wherein the allergy-specific degranulation stimulation factor is present in an amount of from 0.01 to 100 mg/l.

13. The process of claim 1 wherein the degranulation stimulation factor is present in an amount of from 1 to 10 mg/l.

14. The process of claim 1 wherein the incubation period is about 15 to 60 minutes and the incubation is carried out at a temperature of from 20° to 37° C.

15. The process of claim 14 wherein the allergy-specific degranulation stimulation factor is present in an amount of from 0.01 to 100 mg/l.

16. A reagent comprising a buffer with a pH of from 6.3 to 9, an allergy-specific degranulation stimulation factor in an amount of from 0.01 to 100 mg/l, a calcium salt in a concentration of from 0.5 to $5 \times 10^{-3}$ mol/l and a chromogen present in a concentration of $10^{-4}$ to $10^{-3}$ mol/l, said chromogen being capable of forming a chromophor with an allergy specific protease liberated from human leukocytes of a sample in response to said allergy-specific degranulation stimulation factor.

17. The reagent of claim 16 wherein the stimulation factor is present in an amount of from 1 to 10 mg/l.

18. A test device for detection of an allergy or of an allergy-specific degranulation stimulation factor comprising a microtiter plate having a plurality of wells wherein each well contains a buffer with a pH of from 6.3 to 9, an allergen or other allergy-specific degranulation stimulation factor in an amount of from 0.1 to 100 mg/l, a calcium salt in a concentration of from 0.5 to $5 \times 10^{-3}$ mol/l, and a chromogen, said chromogen present in a concentration of $10^{-4}$ to $10^{-3}$ mol/l and capable of reacting with an allergy-specific protease liberated from human leukocytes in response to said allergen or other allergy-specific degranulation stimulation factor.

19. A process for determining an anti-allergic and anti-inflammatory substance useful in treating a specific allergy comprising first incubating a suspension of $10^9$ to $10^{10}$ per liter of human leukocytes for 5 to 60 minutes at a temperature of 20°-37° C. with the anti-allergic and anti-inflammatory substance to be tested, thereafter adding a reagent containing, in an aqueous medium (a) a buffer with a pH from 6.3 to 9, (b) 0.5 to $5 \times 10^{-3}$ mol/l of calcium ions, (c) 0.01 to 100 mg/l of a degranulation stimulation factor specific for said allergy, wherein an allergy-specific protease is liberated from said human leukocytes in response to said degranulation factor and (d) $10^{-4}$ to $10^{-3}$ mol/l of a chromogen in isotonic solution wherein said chromogen specifically reacts with the liberated allergy-specific protease to form a chromophor, incubating for a second period of time sufficient to liberate said allergy-specific protease, kinetically measuring the formation of said chromophor and comparing said chromophor formation with that obtained from a control suspension without the anti-allergic and anti-inflammatory substance thereby determining the presence and quantity of said substance.

20. The process of claim 19, wherein the first incubation is carried out for 30 minutes.

21. The reagent of claim 16 wherein said allergy-specific degranulation stimulation factor is an allergen.

22. The reagent of claim 21 wherein the allergen is present in an amount of from 1 to 10 mg/l.

23. The process of claim 3 wherein said degranulation stimulation factor is an allergen.

24. A test device comprising an absorbent carrier, a swellable synthetic resin film or a gel which is impregnated with the reagent according to claim 16.

25. The process according to claim 1 or 3 wherein the incubation step comprises dipping the test device of claim 24 into the leukocyte suspension and the determining step comprises measuring chromophor formation on said test device.

26. The process of claim 8 wherein the aqueous medium additionally contains a cell-stabilizing amount of gelatin.

* * * * *

UNITED STATES PATENT AND TRADEMARK OFFICE
CERTIFICATE OF CORRECTION

PATENT NO. : 5,116,731

DATED : May 26, 1992

INVENTOR(S) : Otto-Henning Wilhelms

It is certified that error appears in the above-identified patent and that said Letters Patent is hereby corrected as shown below:

Col. 7, line 7: after "TRIS" insert -- [2-amino-2-(hydroxymethyl)-1,3-propandiol] --.

Signed and Sealed this

Twenty-first Day of December, 1993

Attest:

BRUCE LEHMAN

Attesting Officer     Commissioner of Patents and Trademarks